US008629110B2

(12) United States Patent
Heras Fortuny et al.

(10) Patent No.: US 8,629,110 B2
(45) Date of Patent: Jan. 14, 2014

(54) KV1.3 CHANNEL BLOCKING SUBSTANCES FOR THE TREATMENT OF DISEASES ASSOCIATED WITH INTIMAL HYPERPLASIA (75) Inventors: M' Magdalena Heras Fortuny, Barcelona (ES); Mercé Roqué Moreno, Barcelona (ES); M' Teresa Pérez García, Valladolid (ES); José Ramón López López, Valladolid (ES); Pilar Cidad Velasco, Valladolid (ES)

(73) Assignees: Hospital Clinic I Provincial de Barcelona, Barcelona (ES); Universidad de Valladolid, Valladolid (ES)

( * ) Notice: Subject to any disclaimer, the term of this patent is extended or adjusted under 35 U.S.C. 154(b) by 112 days.

(21) Appl. No.: 13/123,220

(22) PCT Filed: Oct. 8, 2009

(86) PCT No.: PCT/EP2009/063099
§ 371 (c)(1),
(2), (4) Date: Jul. 20, 2011

(87) PCT Pub. No.: WO2010/040803
PCT Pub. Date: Apr. 15, 2010

(65) Prior Publication Data
US 2011/0275571 A1 Nov. 10, 2011

(30) Foreign Application Priority Data
Oct. 8, 2008 (EP) ..................... 08105518

(51) Int. Cl.
A61K 38/00 (2006.01)
A61K 38/16 (2006.01)
C07K 14/00 (2006.01)

(52) U.S. Cl.
USPC .......... 514/17.4; 514/21.3; 530/300

(58) Field of Classification Search
None
See application file for complete search history.

(56) References Cited

U.S. PATENT DOCUMENTS 5,116,864 A 5/1992 March et al.
5,354,774 A 10/1994 Deckelbaum et al.

FOREIGN PATENT DOCUMENTS

WO   WO 93/07748      4/1993
WO   WO 97/05127      2/1997
WO   WO 2008/088422   7/2008

OTHER PUBLICATIONS

Olschewski, A. (2011). Cardiovascular Research. 89:255-257.*
Abdel-Mottaleb, et al., "OdK2, a Kv 1.3 channel-selective toxin from the venom of the Iranian scorpion *Odonthobuthus doriae*" *Toxicon*(2008) 51: 1424-1430.
Aranda, J.M. Jr. and J. Hill, "Cardiac Transplant Vasculopathy" *Cardiac Transplant Vasulopathy. Chest.* (2000) 118(6): 1792-1800 (Abstract only).
Bhardwaj, et al., "Gene therapy to prevent occlusion of venous bypass grafts" *Expert Rev. Cardiovasc Ther.* (2008) 6(5): 641-652 (Abstract only).
Cahalan, et al., "Molecular Properties and Physiological Roles of Ion Channels in the Immune System" *J. Clinical Immunology* (2001) 21(4): 235-252.
Chandy, et al., "$K^+$channels as targets for specific immunomodulation" *TRENDS in Phama. Sci.* (2004) 25(5): 280-289.
Cheong, et al., "Blockers of $K_v1.3$ channel suppress smooth muscle response to injury and neointimal hyperplasia" *The FASEB J.* (2007) 21: 121.9 (Abstract only).
Davies, M.G. and P.O. Hagen, "Pathobiology of intimal hyperplasia" *Br. J. Surg.* (1994) 81(9): 1254-1269 (Abstract only).
Gallo, et al., "Prolonged Thrombin Inhibition Reduces Restenosis After Balloon Angioplasty in Porcine Coronary Arteries" *Circulation* (1998) 97: 581-588.
Grissmer, et al., "Expression and chromosomal localization of a lymphocyte $K^+$channel gene" *PNAS USA* (1990) 87: 9411-9415.
Grissmer, et al., "Pharmacological characterization of five cloned voltage-gated K+ channels, types Kv1.1, 1.2, 1.3, 1.5, and 3.1, stably expressed in mammalian cell lines" *Mol. Pharmacol.* (1994) 45(6): 1227-1234 (Abstract only).
Hu et al., "Characterization of the Functional Properties of the Voltage-Gated Potassium Channel $K_v1.3$ in Human $CD4^+T$ Lymphocytes" *J. Immunol.* (2007) 179: 4563-4570.
Jackson, William F., "Potassium Channels in the Peripheral Microcirculation" *Microcirculation* (2005) 12(1): 113-127.
Miguel-Velado, et al., "Contribution of Kv Channels to Phenotypic Remodeling of Human Uterine Artery Smooth Muscle Cells" *Circulation Research* (2005) 97: 1280-1287.
Murphy, Gavin J. and Gianni D. Angelini, "Insights into the pathogenesis of vein graft disease: lessons from intravascular ultrasound" *Cardiovascular Ultrasound* (2004) 2(8): 1-6.
Roque, et al., "Mouse Model of Femoral Artery Denudation Injury Associated with the Rapid Accumulation of Adhesion Molecules on the Luminal Surface and Recruitment of Neutrophils" *Arterioscler Thromb Vasc Biol* (2000) 20: 335-342.
Schmauss, Daniel and Michael Weis, "Cardiac Allograft Vasculopathy: Recent Developments" *Circulation* (2008) 117: 2131-2141.
Schmitz, et al., "Design of PAP-1, a Selective Small Molecule Kv1.3 Blocker, for the Suppression of Effector Memory T Cells in Autoimmune Diseases" *Mol. Pharmacol.* (2005) 68(5): 1254-1270.

(Continued)

*Primary Examiner* — Christine J Saoud
*Assistant Examiner* — Jon M Lockard
(74) *Attorney, Agent, or Firm* — Knobbe, Martens, Olson & Bear LLP (57) ABSTRACT

The present invention provides a therapeutic tool against intimal hyperplasia consisting of the use of Kv1.3 channel blocking substances, able to selectively stop cell migration and multiplication of VSMCs.

9 Claims, 9 Drawing Sheets

(56) References Cited

OTHER PUBLICATIONS

Shijin, et al., "Characterization of a new Kv1.3 channel-specific blocker, J123, from the scorpion *Buthus martensii* Karsch" *Peptides* (2008) 29: 1514-1520.

Weiss, et al., "Mechanisms of Chronic Rejection in Cardiothoracic Transplantation" *Front Biosci*. (2010) 13: 2980-2988.

Wulff, et al., "Potassium channels as therapeutic targets for autoimmune disorders" *Curr. Opin. Drug. Discov. Devel*. (2003) 6(5): 640-647.

International Search Report dated Mar. 31, 2010, issued in International Application No. PCT/EP2009/063099.

Written Opinion dated Aug. 24, 2010, issued in Spanish Patent Application No. 200900281, and English Translation.

* cited by examiner

KV1.3 CHANNEL BLOCKING SUBSTANCES FOR THE TREATMENT OF DISEASES ASSOCIATED WITH INTIMAL HYPERPLASIA

RELATED APPLICATIONS

This application is a U.S. National Phase of International Application No. PCT/EP2009/063099, filed Oct. 8, 2009, designating the U.S. and published on Apr. 15, 2010 as WO 2010/040803, which claims priority to European Patent Application No. 08105518.8, filed Oct. 8, 2008. The content of these applications is incorporated herein by reference in its entirety.

FIELD OF THE INVENTION

The present invention is comprised in the field of cardiovascular pathologies, particularly in the field of diseases derived from the hyperplasia of the tunica intima.

BACKGROUND OF THE INVENTION

The wall of blood vessels is made up of three concentric strata or tunicae (the tunica intima, media and adventitia) with well distinguished structure and composition. The tunica intima is made up of a single layer of endothelial cells supported on a basement membrane rich in collagen and proteoglycans and separated from the media by the internal elastic lamina. The tunica media is formed by vascular smooth muscle cells (VSMCs) and extracellular matrix, and the adventitia, the outermost layer, is essentially made up of connective tissue and fibroblasts.

The VSMCs are physiologically located in the tunica media. However, VSMCs can be found in the intimal layer as a result of a lack of organization of the structure of the vascular wall due to vascular pathologies or lesions such as atherosclerosis, hyperplasia of the tunica intima.

Intimal hyperplasia is a change in the vascular structure which occurs as a result of the biological repair mechanisms after a vascular lesion, either mechanical, surgical, inflammatory or immunological. The most characteristic finding of this structural change is the thickening of the intimal layer, due both to an increase in the number of cells and to an increase in the synthesis of extracellular matrix in which these cells are found (Davies M G, Hagen P O. *Pathobiology of intimal hyperplasia. British Journal of Surgery* 1994; 81:1254-1269). Ultimately, this process results in narrowing or stenosis of the vascular lumen.

There are various pathological situations associated with intimal hyperplasia and the triggering factors can generally be grouped together as physical lesions (in many cases iatrogenic lesions due to vascular surgery), inflammatory lesions (as in atherosclerotic lesions) or due to an increase of the tension of the wall (as in the case of pulmonary hypertension or the use of vein grafts in by-pass surgery). Some of the diseases associated with intimal hyperplasia include:

Late By-Pass Occlusion:

Revascularization with vein grafts is the standard treatment for occlusive arterial diseases when the occluded segment is large and an endarterectomy cannot be performed. The most used technique is the autogenic transplant of a segment of the saphenous vein, and it is used both in coronary surgery and in peripheral vascular surgery (intermittent claudication, thromboangiitis obliterans of the tibial artery, etc.). Although the procedure has a very good immediate result, in the long term, the vein graft suffers chronic maladaptive response to an arterial environment in which the primary component is the uncontrolled proliferation of vascular smooth muscle cells, giving rise to intimal hyperplasia which can later become complicated due to the development of atherosclerosis and thrombosis (Murphy G J, Angelini G D. *Cardiovasc Ultrasound* 2004; 21:2-8). The possibility of handling ex vivo vein transplants prior to their implantation using pharmacological methods, gene therapy or the application of synthetic coatings is an alternative that has been attempted to be used to prevent vascular graft failure (Mann M J, Whittermore A D, Donaldson M C, et al., Lancet 1999; 354: 1493-8; Bhardwaj S, Roy H, Ylä Herttuala, Expert Rev Cardiovasc Ther 2008; 6:641-52) and which in some cases has proven to be effective in experimental animals.

Post-Transplant Coronary Vasculopathy:

Post-transplant coronary vasculopathy is the main factor limiting long-term survival after a heart transplant. It manifests as an especially aggressive form of coronary artery disease that is different from conventional arteriosclerosis, which is caused by the combination of physical, chemical and immunological factors causing an endothelial lesion which in turn triggers the proliferation of vascular smooth muscle cells and intimal hyperplasia The pathological analysis of the lesions shows a thickening of the intima in which undifferentiated cells of the smooth muscle and macrophages and lymphocytes participate. This thickening of the intima leads to the obstruction of the coronary arteries, which ultimately leads to graft failure (Aranda and Hill, *Chest* 2000, 118(6): 1792-1800; Schmauss and Weis, *Circulation* (2008) 117(16):2131-41M: Weiss et al., *Front Biosci*. (2008) 13:2980-8).

An important aspect of the pathogenesis of vasculopathy is the interaction of immunological and non-immunological factors. In fact, for many years it was believed that intimal hyperplasia was due exclusively to immunological factors. However, immunosuppressant therapies have not been proven to be capable of reducing its incidence. On the contrary, an increase of hyperplasia after the introduction of treatments based on the use of immunosuppressants, such as cyclosporine, has been observed. In studies conducted with experimental animal models, promising results have been obtained when these immunosuppressant agents are combined with drugs such as MMF (mycophenolate mofetil) which inhibits DNA synthesis and therefore has a generalized antiproliferative effect that extends beyond the immune cells. Although revascularization procedures (percutaneous coronary angioplasty, coronary atherectomy, coronary bypass surgery or stent implantation) can be used in patients presenting localized stenoses, the diffuse character of arteriopathy makes the use of these therapies limited; therefore the development of new pharmacological therapies targeted at controlling the factors which determine intimal hyperplasia in this vasculopathy is necessary.

Post-Transplant Chronic Nephropathy:

The factors triggering coronary vasculopathy are also present in other post-transplant vasculopathies, as is the case of post-transplant nephropathy, which again represents the most frequent cause of renal transplant failure.

In addition to those mentioned, there are other diseases resulting from intimal hyperplasia. In order to identify when a disease is due to intimal hyperplasia, the person skilled in the art will use imaging techniques. Specifically, coronary angiography is used in the coronary tree, injecting contrasting fluid into the ostium of said arteries. Likewise, the 64-slice multislice CT and cardiac resonance angiography are also able to display atherosclerotic lesions in the coronary circulation.

Figure 1:
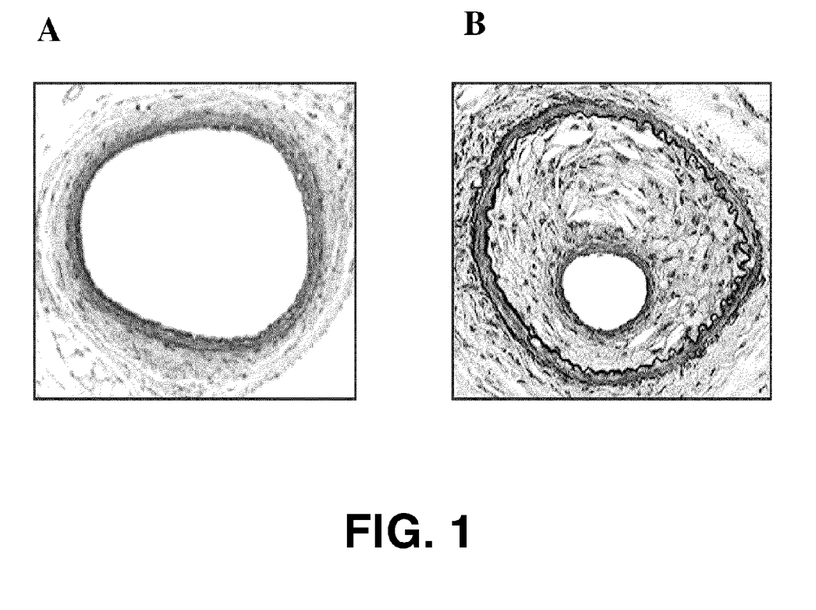
FIG. 1A shows a representative microphotograph of sections of a normal artery.
FIG. 1B shows a representative micrograph of an artery with intimal hyperplasia, in which the greater density of smooth muscle cells in the arterial wall can be seen.

Angiographic techniques are complemented with ultrasound techniques, such as intravascular ultrasound, which allow displaying the thickness of the arterial intimal layer, and determining if there is an atherosclerotic lesion and its characteristics. In normal conditions, the thickness of the intima cannot be measured microscopically because it is a single layer of cells. However, any measurable thickness (which is greater than a single cell layer) is pathological (FIG. 1).

Figure 2:
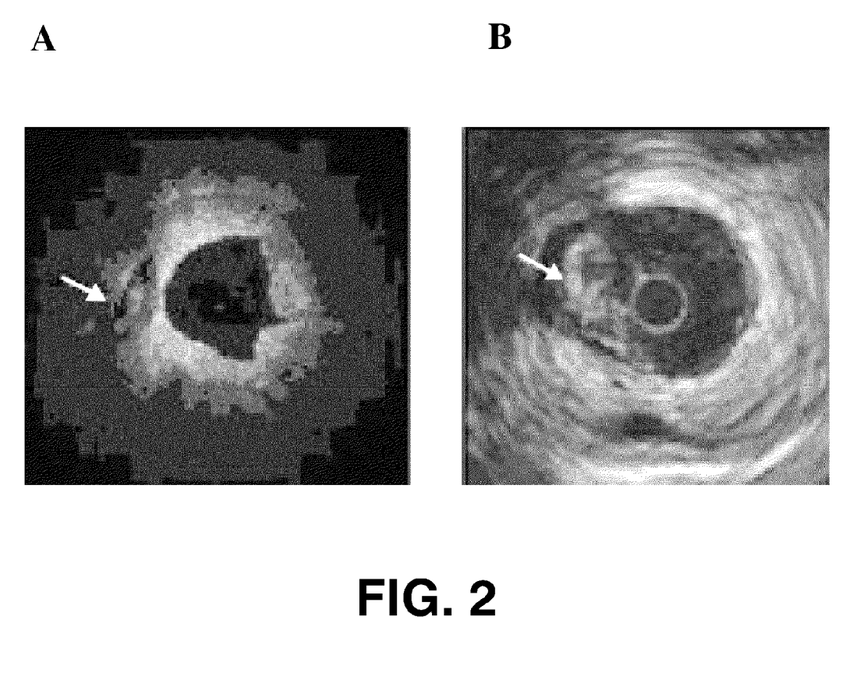
FIGS. 2A and 2B show OCT (optical coherence tomography) micrographs identifying areas of intimal hyperplasia by means of laser technology.

There are other techniques, such as virtual histology, which allows determining the presence of lipids, calcium, a clot, fibrous tissue and hyperplasia, and OCT (optical coherence tomography), which uses laser technology to determine the entire thickness of the vascular wall and thus identifying the areas of intimal hyperplasia (see FIG. 2). Both in human arterial specimens and in experimental samples of animal models, morphometry is used for the histological analysis of the thickness of the various layers of the arterial wall. After the suitable treatment period, the animal will be euthanized and the studied vessels extracted and fixed for their subsequent analysis. Histological slices will be obtained and stained with hematoxylin-eosin. The internal elastic lamina will be identified and the areas of the various vascular layers evaluated (Gallo et al., 1998 *Circulation* 97:581-588)

Given the incidence and severity of these pathologies, there is a need to develop a tool which limits or prevents intimal hyperplasia and the pathological situations resulting from it, especially after surgical interventions or transplant surgery.

The inventors have surprisingly found that the 1.3 voltage-activated potassium channel (Kv1.3) blockers significantly limit intimal hyperplasia.

Traditionally, inhibitors of Kv1.3 have been used in therapies against immunological diseases, such as encephalomyelitis or multiple sclerosis (Wulff, H. et al., 2003. *Curr. Opin. Drug Discov. Devel.* 6: 640-647. Cahalan, M. D., et al., 2001. *J. Clin. Immunol.* 21:235-252). Kv1.3 was first identified in T-cells (Hu et al., *The Journal of Immunology*, 2007, 179: 4563-4570. Grissmer et al., *Proc. Nat. Acad. Sci.* 87: 9411-9415, 1990). In these cells, the Kv1.3 channel is tetra-homomeric, whereas in other types of cells, Kv1.3 is associated with subunits of other voltage-activated channels of the Kv1 family to form heteromeric potassium channels (Hu et al., *The Journal of Immunology*, 2007, 179: 4563-4570). As a consequence, the regulation of K⁺ flows through the membrane of the cells is often the combinatorial result of multiple molecular signaling pathways. The importance of Kv1.3 in immune system-related diseases has been proven in several studies.

Document WO2008088422 discloses the use of peptide inhibitors of Kv1.3 for the treatment of autoimmune diseases, allergies, diabetes and obesity and describes the manufacture and purification of derivatives of the toxins ShK, $MgTx_1$, $MTX_1$, HsTxl, wGVIA, HaTxl, etc. According to the data shown, the peptide derivatives of ShK are able to inhibit the human Kv1.3 current with an IC of −150 pM. ShK is, furthermore, a potent inhibitor of the proliferation of T-cells so their use in therapies for the treatment of immunological diseases such as multiple sclerosis, rheumatoid arthritis, dermatitis, diabetes type I, etc., is proposed.

K⁺ Channels in the Vascular Smooth Muscle

Potassium channels also play a very relevant role in the immediate and long-term regulation of the function of the vascular smooth muscle cells. The VSMCs of the walls of the vessels are cells which express a unique repertoire of contractile proteins, ion channels and signaling molecules aimed at maintaining vascular tone. At least four types of K⁺ channels have been identified in VSMCs: voltage-dependent K⁺ channels (Kv), such as Kv1.2, Kv1.3, Kv1.5, Kv1.6 and Kv2.1, calcium-activated K⁺ channels (such as the maxiK or BK channels), of inward-rectifying K⁺ channels (such as the $K_{IR}$ channels and $K_{ATP}$ channels) and two-pore K⁺ channels, which are responsible for the background currents and the TASK and TWIK channels (reviewed in Jackson W F, *Microcirculation* 12, 113-127, 2005). Furthermore, the existence of regulating subunits of these channels together with the variation in their expression depending on the vascular bed, contributes to the fine regulation of the smooth muscle physiology. Thus, the pathological processes can be associated with the deregulation of multiple control mechanisms acting in parallel or in combination. Determining which mechanism leads to a specific vascular disease is an arduous scientific experiment task.

According to the foregoing, and due to the diffuse and distal location of hyperplastic lesions, the field of the art cannot provide effective therapies for the treatment of intimal hyperplasia. It would therefore be convenient to develop a therapeutic tool aimed at controlling the factors determining hyperplasia of the tunica intima and which is able to stop the migration and proliferation of the VSMCs therein, as well as the secretion of components of the cell matrix.

BRIEF DESCRIPTION OF THE DRAWINGS

FIG. 1.

FIG. 2.

FIG. 3. Example of the assay for determining if a substance is a Kv1.3 channel blocker. Panel A shows strokes representing the currents evoked by the different depolarizing pulses (from −60 to +80 mV) in a HEK cell transfected with the Kv1.3 channel, in control recording conditions, in the presence of 10 nM of PAP-1 in the solution of the bath and after washing the drug. The lower diagram shows the pulse protocol scheme applied. The amplitude of the maximum current evoked by each voltage pulse is depicted in panel B depending on the value of the membrane potential, with which the current (I) voltage (V) curve is constructed for the three situations.

FIG. 6. Characterization of the functional expression of the Kv1.3 channels. The upper part shows records representing currents induced by the application of a depolarizing pulse from a resting potential of −80 mV up to a potential of +40 mV in control conditions and in the presence of a Kv1.3 channel blocker, Margatoxin, at a concentration of 10 nM. Representative strokes obtained in a VSMC freshly dissociated from the wall of the artery (contractile) and in a VSMC in culture are shown. The lower panel shows the means (±standard error of the mean) obtained in 10-12 cells in each group in which selective Kv1.3 channel blockers and 10 nM margatoxin or 10 nM PAP-1 were applied as well as blockers of all Kv1 channels (such as correolide).

FIG. 7. Effect of the Kv1.3 channel blockers on the migration of VSMCs of the human uterine artery. The left panels show photographs representing the migration observed in control cultures and cultures treated with the indicated drugs. The irregular surface created by the dotted line has been drawn surrounding the cell-free area at time 0, and this same surface has been transposed to the culture after 24 hours to offer a visual estimate of the invaded area in each of the three examples. The results obtained in 8-10 similar experiments have been expressed as a percentage of the area at time 0 which is covered with cells at 24 hours and are shown in the right part of the drawing (* $p<0.05$; ** $p<0.01$).

FIG. 8. Effect of the Kv1.3 channel blockers on the proliferation of the VSMCs of the human uterine artery. The drawing shows a representative example in which photos taken with the DAPI labeling (to count the number of cells) and the same field with the BrdU labeling (to determine the number of proliferating cells) are shown. Again, these experiments were conducted in cells in control medium and cells in which the margatoxin or PAP was added to the medium. As is seen in the example, in these last two cases a lower number of labeled nuclei is observed. The quantification of 8-12 fields in 6 different experiments indicated that these variations were statistically significant. The bar chart on the right shows the means of these experiments (** $p<0.01$)

SUMMARY OF THE INVENTION

According to the need to develop a tool for an effective therapy against hyperplasia of the vascular tunica intima, the inventors propose the use of Kv1.3 channel blocking substances in the manufacture of a pharmacological tool for the treatment of diseases relating to intimal hyperplasia.

An advantage of the present invention is the selective blocking of the Kv1.3 channels of the VSMCs by means of the use of blocking substances belonging to the group of margatoxin, ShK toxin, psoralen, kaliotoxin, correolide, J123, and the derivatives and combinations thereof, for the manufacture of a pharmacological tool for the treatment of diseases relating to hyperplasia of the vascular tunica intima. According to this, a possible embodiment of the present invention is the use of Kv1.3 blockers in the manufacture of a pharmacological tool for the treatment of vascular diseases which cause restenosis and comprise post-transplant chronic nephropathy, late by-pass occlusion and post-transplant coronary vasculopathy, and the equivalents and combinations thereof. In particular, the present invention comprises the use of Shk-L5, PAP-1 or both, in the manufacture of a pharmacological tool for the treatment of said vascular diseases. An advantageous embodiment of the present invention is the use of said blocking substances in the manufacture of a pharmacological tool for the treatment and/or prevention of restenosis.

Clinical practice would benefit from the application of a preventive and/or therapeutic protocol against hyperplasia of the tunica intima. Accordingly, a possible embodiment of the present invention consists of a method for the prevention or treatment of intimal hyperplasia, comprising the administration of a Kv1.3 blocking substance. Advantageously, this method is used for the selective blocking of the Kv1.3 channels of the VSMCs by means of the use of pharmacological tools manufactured with blocking substances belonging to the group of margatoxin, ShK toxin, psoralen, kaliotoxin, correolide, J123, and the derivatives and combinations thereof, preferably Shk-L5, PAP-1 or both. In particular, this method can be applied in the treatment of diseases which cause restenosis, such as post-transplant chronic nephropathy, late by-pass occlusion and post-transplant coronary vasculopathy, and the equivalents and combinations thereof.

Cardiovascular pharmacology lacks effective tools designed for the treatment of diseases resulting from hyperplasia of the tunica intima. For the purpose of solving this lack, a possible embodiment of the present invention consists of a metering apparatus for implanting in an arterial vessel of an animal, which can be a human, comprising a containing system for containing a Kv1.3 blocking substance. An advantage of this apparatus is that the active ingredient it meters is a selective Kv1.3 channel blocker of the VSMCs belonging to the group of margatoxin, ShK toxin, psoralen, kaliotoxin, correolide, J123, and the derivatives and combinations thereof. The present invention preferably comprises the substances Shk-L5, PAP-1 or both. In particular, this apparatus can be applied in the treatment of diseases which cause restenosis, such as post-transplant chronic nephropathy, late by-pass occlusion and post-transplant coronary vasculopathy.

DETAILED DESCRIPTION OF THE INVENTION

The inventors propose the use of Kv1.3 blocking substances, as described below, for the treatment of the diseases resulting from the thickening of the intima.

The invention is based on the discovery that the smooth muscle cells located in the intimal hyperplasia preferably express Kv1.3 (FIGS. 3, 4, 5 and 6) and that by using blocking substances specific for the Kv1.3 channels, the rate of cell division and migration of the VSMCs (FIGS. 7 and 8) and the subsequent thickening of the intima after a vascular lesion are reduced.

According to the present invention, the Kv1.3 channel blocking substances can be used as pharmacological tools for the treatment of vascular diseases. In the context of the present invention, a pharmacological tool is any substance, composition, utensil, device, mechanism, contrivance, contraption, instrument, machine or apparatus adapted, studied or designed to be used in the treatment, cure, prevention or diagnosis of a disease, or to prevent the onset of an unwanted physiological process.

Vascular diseases can be a consequence of the lack of organization of the normal structure of the vascular wall. The three concentric layers of the vascular wall or tunicae can become unorganized during pathological processes or as the consequence of physical lesions, causing the vascular lumen to narrow (FIG. 1). In particular, in many diseases, including post-transplant chronic nephropathy, late by-pass occlusion and post-transplant coronary vasculopathy, the lack of organization of the structure of the vascular wall manifests by means of hyperplasia of the tunica intima (FIG. 1). In the context of the present invention, hyperplasia relates to any assessable thickening of the intimal layer (beyond a single layer of cells). An increase of components of the connective tissue, specifically of the cell matrix, including collagen, proteoglycans and elastic fibers, as well as the increase in the number of mesodermal cells, are observed ultrastructurally in hyperplastic intima. The cells which can be found in the hyperplastic intima include, besides the single layer of endothelial cells, cells from the immune system and cardiovascular smooth muscle cells. The latter, which are absent in the tunica intima in physiological situations, have experienced cell migration and proliferation processes in the tunica intima. Due to this cell activity, which entails the secretion of cell matrix, the mentioned thickening and, accordingly, the reduction of the vascular lumen occur. In the context of the present invention, the term restenosis relates to this reduction in diameter of the vascular lumen. Restenosis is a consequence of the lack of organization of the vascular wall and is therefore common in many vascular diseases, including post-transplant chronic nephropathy, late by-pass occlusion and post-transplant coronary vasculopathy. In the context of the present invention, therefore, diseases equivalent to post-transplant chronic nephropathy, late by-pass occlusion and post-transplant coronary vasculopathy are those which present a lack of organization of the structure of the vascular wall which manifests by means of intimal hyperplasia and causes the vascular lumen to narrow, or restenosis. In the context of the present invention, it is also considered that stenosis and restenosis are equivalent terms and relate to an obstruction ≥50% of the vascular lumen in a given segment.

The guidelines and procedures for the suitable use of Kv1.3 blocking substances in therapies against diseases relating to intimal hyperplasia are explained below. This document includes in its different sections the teachings so that the person skilled in the art can identify this type of disease and the substances acting as Kv1.3 channel blockers. The Kv1.3 channel blockers must be able to decrease in a dose-dependent manner the flow of current through these channels evoked by a depolarizing voltage pulse. The present application describes one of these known methods in Example 1.

In order to prove that a substance acts as a Kv1.3 channel blocker, the person skilled in the art uses a heterologous expression system. Some stable cell lanes expressing the Kv1.3 channel have been described and are available in the field of the art, for example those described in Grissmer et al., *Mol. Pharmacol* 44, 1227-34, 1994. These or other equivalent cells can be requested from their inventors.

Alternatively, the person skilled in the art knows the suitable techniques for developing a heterologous expression system in mammals. To that end, a cell line can be purchased from the ATCC cell collection, such as for example HEK293 cells (Human Embryonic Kidney, catalogue no. ATCC CRC-1573), CHO-K1 cells (Chinese Hamster Ovary, catalogue no. ATCC CCL-61) or COS-7 cells (monkey kidney fibroblasts catalogue no. ATCC CRC-1651) marketed in Europe through LGC Standards, UK. By way of example, the Kv1.3 channel can be expressed in HEK293 cells by means of transfection with Lipofectamine of a suitable plasmid for expression in mammals, which contains the cDNA of the encoding sequence of the Kv1.3 channel. Optionally, the person skilled in the art can perform co-transfection with marker molecules to identify the cells which effectively express the transfected channel.

The use of experiments such as the one described in Example 1 has allowed in the field of the art the identification of a large number of compounds described as Kv1.3 channel blockers. Some of these compounds and their respective affinities for the Kv1.3 channel are specified in Table 1:

TABLE 1

Kd values for Kv1.3 channel blocker peptides and small molecules.

| Blocking substance | Affinity (Kd) |
|---|---|
| Stichodactyla helianthus toxin (ShK) | 11 pM |
| Heterometrus spinifer toxin 1 | 12 pM |
| ShK-F6CA | 48 pM |
| Pandinus imperator toxin 2 | 50 pM |
| ShK-Dap22 | 52 pM |
| Hongotoxin | 86 pM |
| Margatoxin | 110 pM |
| Agiotoxin-2 | 200 pM |
| Pandinus imperator toxin 3 | 500 pM |
| Kaliotoxin | 650 pM |
| Buthus martensii Karsch toxin (J123 peptide) | 790 pM |
| Noxiustoxin | 1 nM |
| Pap-1 | 2 nM |
| Psora-4 | 3 nM |
| Charybdotoxin | 3 nM |
| Titystoxin-Kα | 4 nM |
| Odonthobthus doriae toxin 2 (OdK2) | 7 nM |
| Pandinus imperator toxin 1 | 11 nM |
| Bunodosoma granulifera toxin | 39 nM |
| trans-N-propyl-carbamoyloxy-PAC | 50 nM |
| Correolide | 90 nM |
| Sulfamidbenzamidoindane | 100 nM |
| Maurotoxin | 150 nM |
| CP339818 | 150 nM |
| WIN173173 | 200 nM |
| UK78282 | 200 nM |
| Dendrotoxin | 250 nM |
| PAC | 270 nM |
| Parabuthus toxin 3 | 492 nM |
| Parabuthus toxin 1 | 800 nM |
| Resiniferatoxin | 3 μM |
| Nifedipine | 5 μM |
| Nitrendipine | 5 μM |
| Ibu8 | 5 μM |
| Phencyclidine | 5 μM |
| Verapamil | 6 μM |
| H37 | 10 μM |
| $Hg^{2+}$ | 10 μM |
| Quinine | 14 μM |
| Cicutotoxin | 18 μM |
| $La^{3+}$ | 20 μM |
| Trifluoperazine | 20 μM |
| Capsaicin | 26 μM |
| Diltiazem | 27 μM |
| Progesterone | 30 μM |
| κ-Hefutoxin | 40 μM |
| Luteolin | 50 μM |
| Flecainide | 60 μM |
| 4-AP | 190 μM |
| $Zn^{2+}$, $Co^{2+}$ | 200 μM |
| $Ba^{2+}$, $Cd^{2+}$ | 2 mM |
| TEA | 10 mM |
| $Mn^{2+}$ | 20 mM |

Abbreviations:
4-AP, 4-aminopyridine;
ShK-Dap22, *Stichodactyla helianthus* toxin with diaminopropionic acid in position 22 substituting a native Lys;
ShK-F6CA, *Stichodactyla helianthus* toxin—fluorescein-6-carboxylic acid;
TEA, tetraethylammonium chloride.
(Data taken from Schimtz et al., *Mol Pharmacol* 2005, 68: 1254-1270; Chandy et al., *TIPS* 2004, 25: 280-288; Abdel-Mottaleb et al., *Toxicon* 2008, 51: 1424-1430; Shijin Yet al., *Peptides* 2008, 29: 1514-1520).

The blockers described above can be used according to the present invention in the manufacture of a pharmacological tool which can commonly be a medicament containing any pharmacologically acceptable excipient and the Kv1.3 blocker as the active ingredient, alone or in combination with other active ingredients. The present invention comprises all the effective doses in any of the comprised diseases as well as any of the possible methods of administration independently of the race, sex, biotype, weight or age of the individual to be treated.

Figure 6:
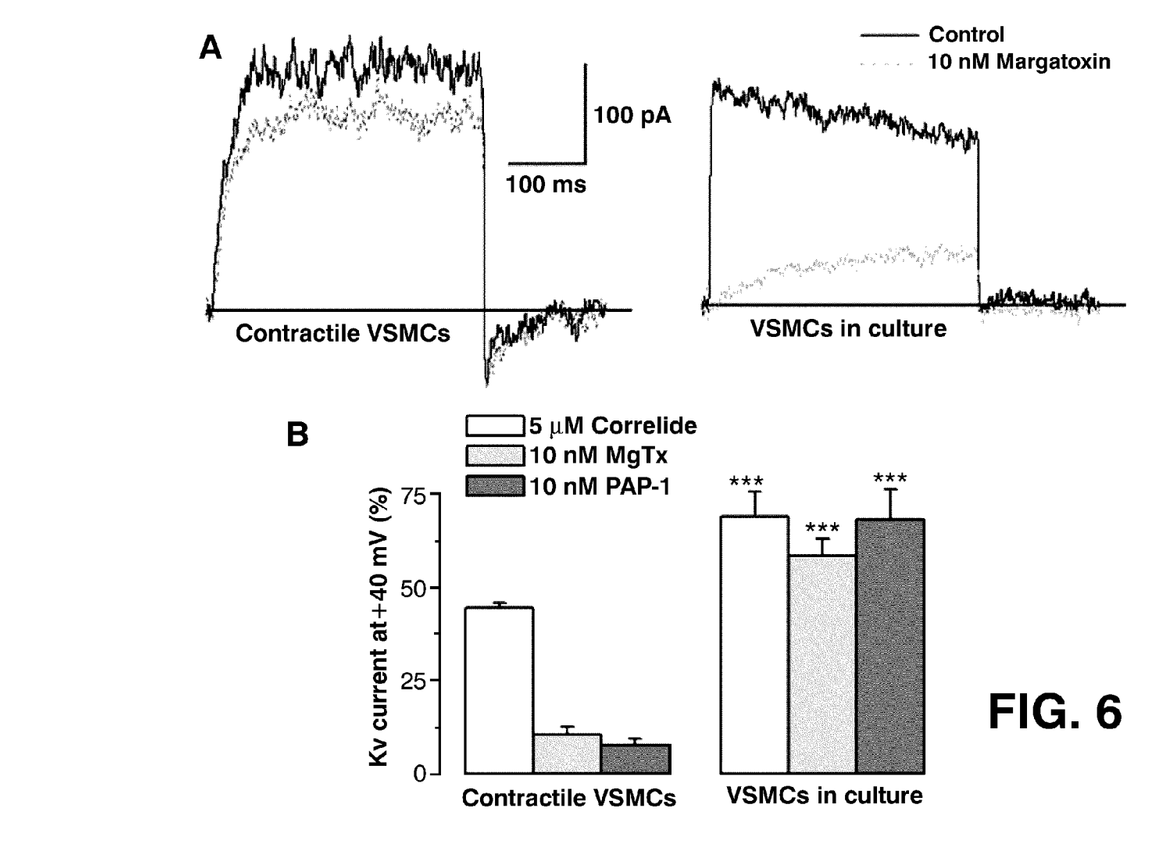
Figure 7:
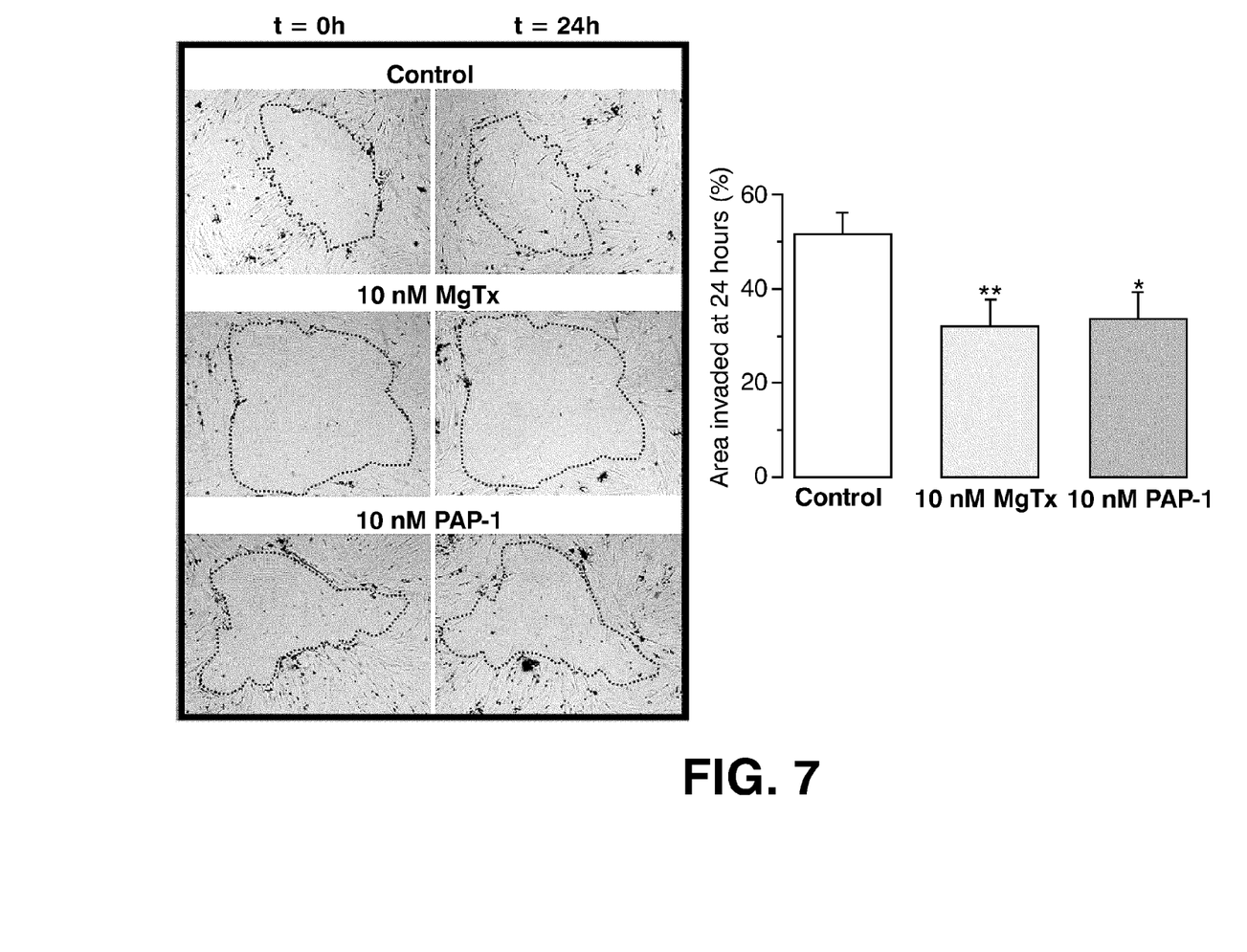
Figure 8:
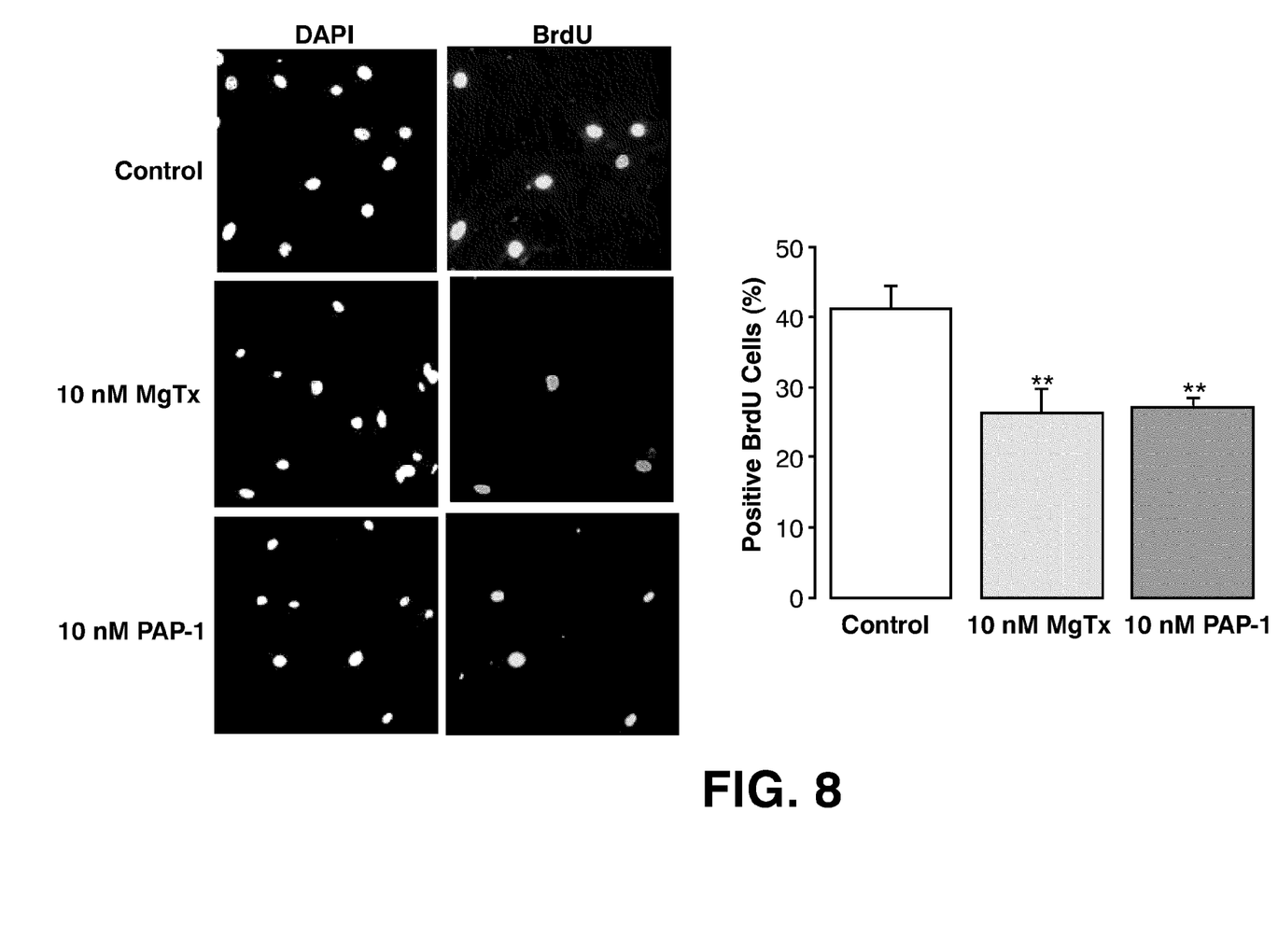

A direct application of the present invention is the development of a new method for the prevention and treatment of vascular diseases which are a consequence of the lack of organization of the normal structure of the vascular wall. This method consists of the administration or the implantation of a pharmacological tool comprising at least one active ingredient having a blocking effect on Kv1.3 channels. Preferably, the method of the present invention consists of the administration of a Kv1.3 channel blocker from the group of margatoxin, ShK toxin, psoralen, kaliotoxin, correolide, J123, and the derivatives and combinations thereof. Very preferably, the blocking substances comprise the ShK-L5 or PAP-1 toxins. Example 4, FIGS. 6, 7 and 8, illustrate the effect of these toxins on the VSMCs and Example 5 describes the administration protocol.

Another important application of the present invention consists of the design and preparation of a system which allows the controlled release of the Kv1.3 blocking substance, such as a stent coated with a biopolymer in which the blocker resides for its gradual release. Example 5 describes the details of this application.

EXAMPLES

Example 1

Assay to Determine if a Substance is a Kv1.3 Channel Blocker

To evaluate if a substance is capable of dose-dependently reducing the flow of current through Kv1.3 (i.e., if it is a Kv1.3 blocker). The currents through the Kv1.3 channels expressed in the heterologous system were studied by means of the patch-clamp technique in the whole-cell configuration. The currents were recorded at room temperature (21-25° C.). The cells, placed in a recording chamber located in an inverted microscope, were perfused with a physiological saline solution (in mM: 141 NaCl, 4.7 KCl, 1.2 $MgCl_2$, 1.8 $CaCl_2$, 10 glucose and 10 HEPES (pH 7.4 with NaOH). The recording pipettes were made from borosilicate glass (2.0 mm OD, WPI) with a pipette puller (Narishige PP-83) so that they have resistances between 2 and 5 MΩ upon filling them with an internal solution containing (in mM) 125 KCl, 4 $MgCl_2$, 10 HEPES, 10 EGTA, 5 MgATP; (pH 7.2 with KOH). The whole-cell currents were recorded with an Axopatch 200 amplifier or the like, filtering at 2 kHz and sampling at 10 kHz. The records were digitalized with a Digidata 1200 A/D interface executed by the CLAMPEX 8 software (Axon Instruments) or an equivalent similar system, in a computer. The cells were maintained at a resting potential of −80 mV and from here depolarizing pulses of 200 ms in duration from −60 mV up to +80 mV in intervals of 10 mV every 15 seconds were applied. Thus the person skilled ion the art can construct a current-voltage curve for the Kv1.3 channel.

Figure 3:
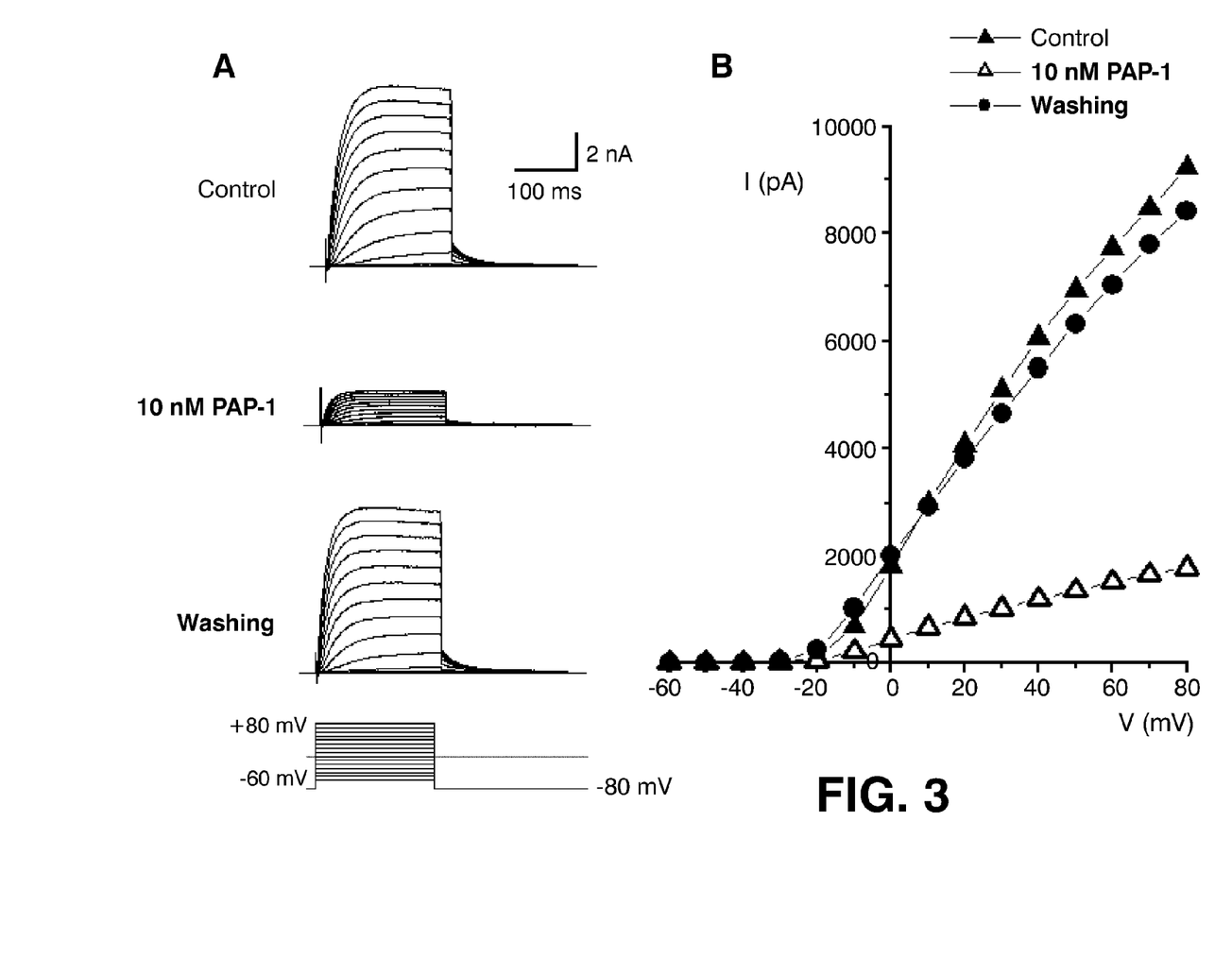

FIG. 3 shows an example of this type of experiment. As can be observed, the application of PAP-1 at a concentration of 10 nM caused a reduction of the current of about 80-85% for potentials from +10 up to +80 mV. The effect of repeated depolarizing pulses from −80 mV up to +40 mV applied every second was evaluated for the purpose of characterizing the characteristic cumulative inactivation of the Kv1.3 currents. The potential blocking substances are applied dissolved in the external solution to study the effect of their application with the protocols previously described and known in the field of the art, such that the possible effects of these substances on the amplitude of the current, the time course and the voltage dependence of their activation and inactivation, can be characterized.

Upon observing modifications in some of these parameters due to the application of a putative blocker, the dose-response curve of the blocking effect, as well as the reversibility of the effect after washing the blocker have to be analyzed. The careful analysis of the rate of the establishment and the washout of the effects allows obtaining an estimate of the affinity constant of the substance to the canal.

By taking the value of the amplitude of the current at a determined voltage (for example +40 mV) in the absence of blocker as the total current (100%), the percent reduction of the amplitude of the current in the presence of the blocker as a value between 0 and 1 (current with substance under analysis in the control medium/current) can be defined. If there is a reduction of the current in the presence of the substance under analysis, a dose-response curve is constructed to define the $IC_{50}$ (or Kd) of the blocking of the Kv1.3 current by the substance under analysis.

To determine the specificity of the substances which are defined, as well as Kv1.3 blockers, the same type of experimental strategy is used.

Example 2

Modification of the Expression of the Kv1.3 Channels in VSMCs of Mouse Femoral Arteries with Proliferative Phenotype The changes in the expression of the Kv1.3 channels were studied by comparing VSMCs of mouse femoral arteries in contractile and proliferative phenotype. The contractile phenotype are the cells isolated directly from the medial layer of the femoral artery, and the effect of the phenotypic change was studied in two different proliferation models: an in vivo model in which intimal hyperplasia is induced by endoluminal lesion with the previously described procedure (Roqué et al., *Arterioscler Thromb Vasc Biol* 20, 335-342, 2000) and an in vitro model in which VSMCs are obtained in culture from explants of mouse femoral artery (Miguel-Velado et al., Circ Res 97, 1280-1287, 2005).

BPN mice were obtained from Jackson Laboratories and maintained by means of inbreeding in the animal house of the School of Medicine or the animal house of the IDIBAPS, in temperature-controlled conditions (21° C.) with 12 hour light/dark cycles and with free access to food and water.

To isolate the VSMCs (model of cells in contractile phenotype), the animals were sacrificed by decapitation after anesthesia with isoflurane (5% at 2.5 l $O_2$ $min^{-1}$). The femoral arteries were dissected and the connective and endothelial tissue was removed and the cells were obtained by means of enzyme dispersion with the previously described protocol (Miguel-Velado et al., Circ Res 97, 1280-1287, 2005).

To obtain the VSMCs in culture (in vitro model of proliferative phenotype), small fragments (0.5 mm) of femoral arteries free of endothelium and connective tissue were placed in 35 mm Petri culture dishes covered with 2% gelatin (Type B, Sigma) in a DMEM culture medium with 20% of fetal bovine serum, 100 U/ml penicillin, 100 U/ml streptomycin and 2 mM L-glutamine at 37° C. in a 5% $CO_2$ atmosphere. The migration and proliferation of the VSMCs of these explants was clear at 6-10 days, but the explants were maintained until the single layer of VSMC was confluent. At this time, by means of mechanical scraping with a rubber spatula the cells were shed and seeded in a new culture dish at ⅓ of their original density. The VSMCs were thus subjected to several passes (3-4) without showing apparent morphological changes.

Finally, for the in vivo proliferation model, the BPN mice were subjected to unilateral transluminal lesion of the femoral artery at the age of 12-16 weeks by means of the repeated pass of an angioplasty catheter 0.25 mm in diameter following the previously described protocol (Roqué et al., *Arterioscler Thromb Vasc Biol* 20, 335-342, 2000). The mice were sacrificed after 48 hours, 1 week or 4 weeks by means of pentobarbital overdose to extract the control and damaged femoral arteries.

Figure 4:
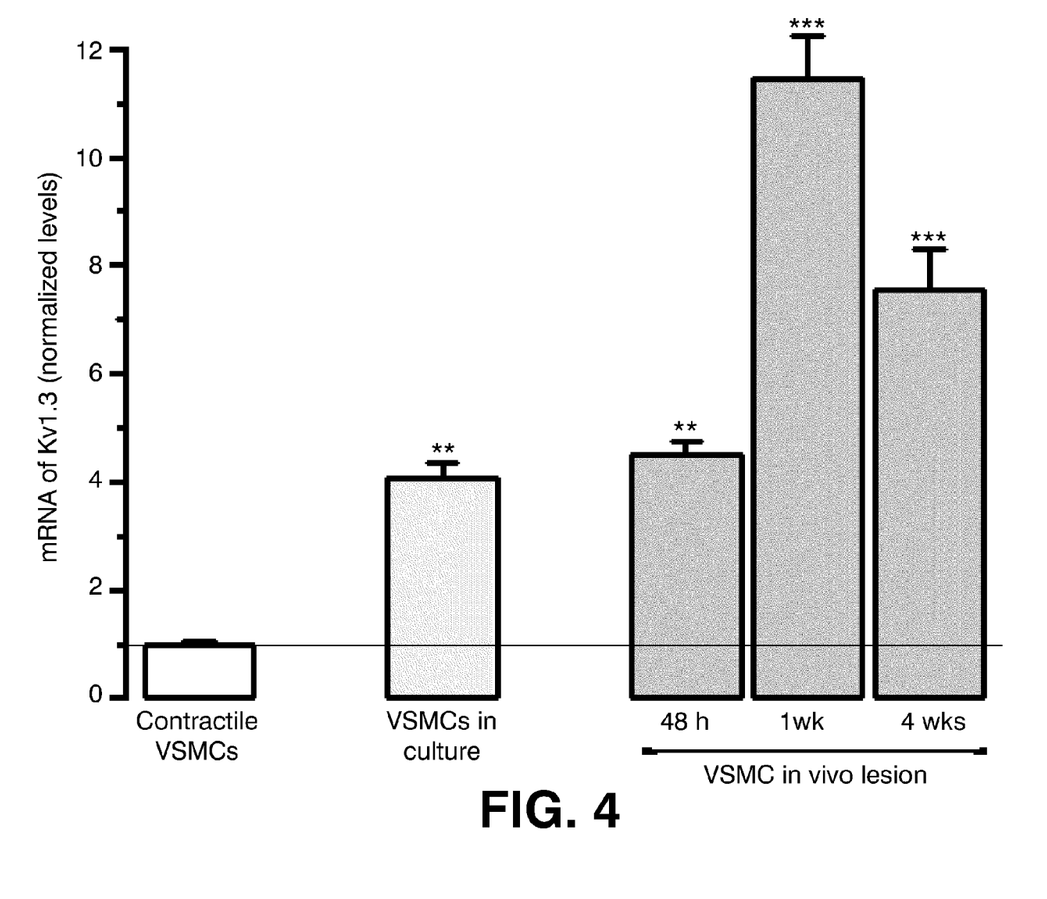
FIG. 4. mRNA levels of the Kv1.3 channel in cells in contractile phenotype and in the two proliferative phenotype models studied. It shows the quantification of the mRNA levels of the Kv1.3 channel obtained in the different preparations with the methods described in the example. The values have been normalized in relation to the expression levels obtained in cells in contractile phenotype. The data show the mean of 3-4 experiments in each situation. ( $p<0.01$; * $p<0.001$).
Figure 5:
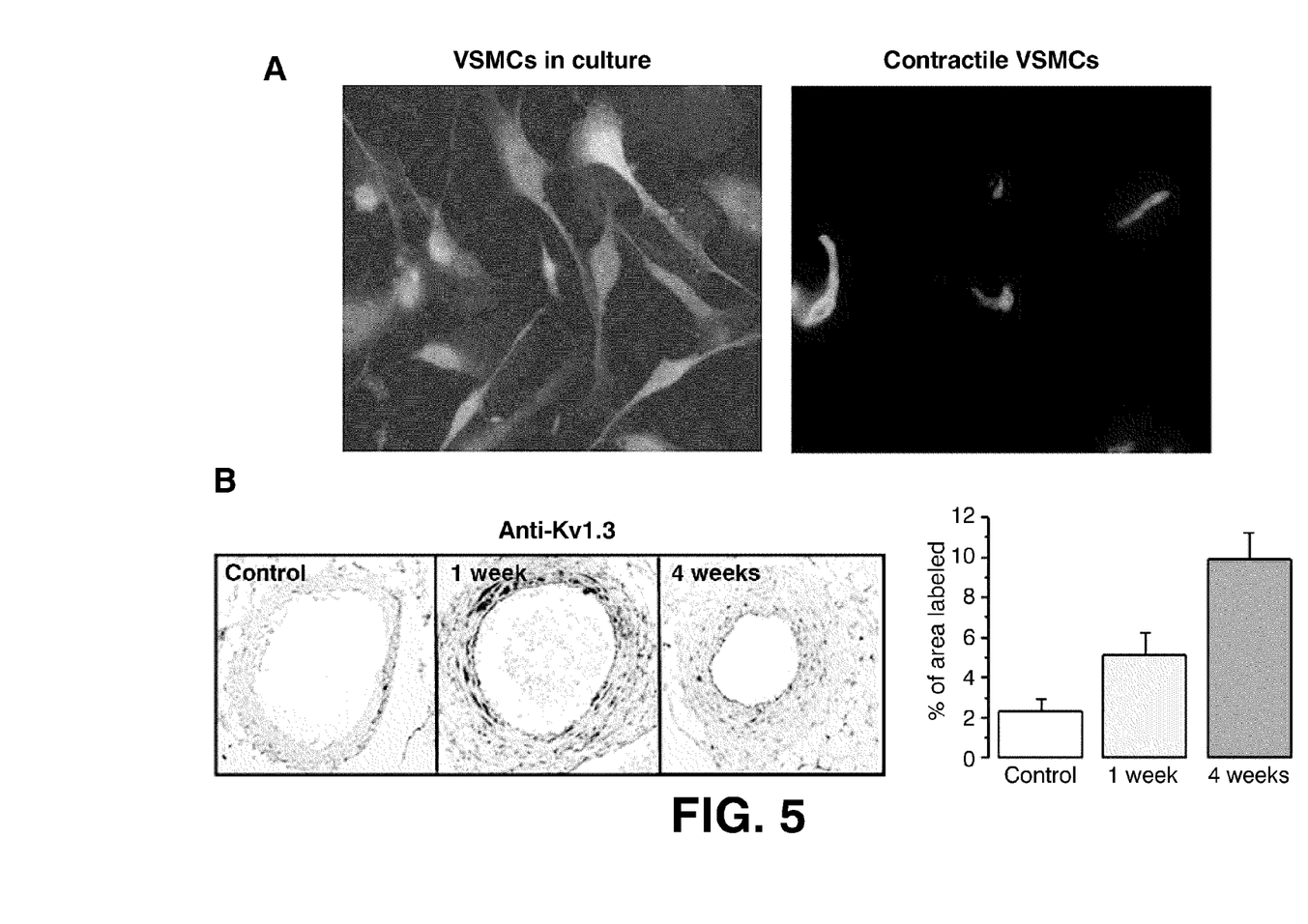
FIG. 5. Expression of the protein of the Kv1.3 channel determined by Immunocytochemistry in isolated cells (panel A) or immunohistochemistry in sections of control and damaged arteries at different times (panel B). Part A shows the labeling of the antibody combined with the labeling of the nuclei with DAPI to estimate the number of cells in the field. Part B shows an example of labeling with anti Kv1.3 antibody as dotting (with a higher intensity of grays-blacks) in an undamaged artery and in an artery damaged at two different times. The bars are the average labeled area (percentage-wise) observed in 15-30 slices in each condition. * $p<0.05$; ** $p<0.01$.

The study of the expression of the Kv1.3 channels in these three experimental preparations was carried out by determining the mRNA levels of the Kv1.3 by means of real time PCR (FIG. 4) and the expression of the protein of Kv1.3 by means of immunohistochemistry in VSMCs in contractile phenotype and VSMCs in culture or immunocytochemistry in femoral artery sections fixed for the in vivo proliferation model with an anti-Kv1.3 antibody (clone L23/27 of Neuromab UC Davis NIH and Antibodies Inc.) and labeled with a fluorescent secondary antibody (FIG. 5). The sample processing and the RNA extraction were performed with the previously described protocols (Miguel-Velado et al., Circ Res 97, 1280-1287, 2005) and the mRNA levels were determined using Taqman probes for Kv1.3 which were obtained from Applied Biosystems.

For the immunocytochemistry with the anti-Kv1.3 antibody, the VSMCs freshly dissociated or in culture were seeded in glass coverslips 12 mm in diameter, fixed with 4% paraformaldehyde in phosphate buffer at pH 7.5 for 15 minutes at 20° C., washed with PBSTx (0.1% PBS Triton X-100) and blocked with PBSTx containing 10 mg/ml of bovine albumin and 2% non-immune goat serum for 10 minutes. The anti-Kv1.3 antibody was diluted in the blocking solution at a concentration of 1:100 for 40-60 min at 21° C. After three 5-minute washings in PBSTx the cells were incubated with the secondary antibody (Alexa 488 goat anti-mouse from Molecular Probes) at a dilution of 1:1000 in blocking solution for 30 minutes. After three other washings with PBSTx the coverslips were assembled with VectaShield H100-DAPI (vector Labs) and the cells were examined in a Nikon fluorescence microscope with a wavelength filter of 488 nm.

For the immunohistochemistry studies, the euthanized animals were fixed with 4% paraformaldehyde intravenous perfusion in PBS for 5 minutes at 100 mmHg to obtain paraffin sections of the femoral arteries as described (Roqué et al., *Arterioscler Thromb Vasc Biol* 20, 335-342, 2000). The sections were subsequently deparaffinized, rehydrated and treated with 1% citric acid and blocked with 3% hydrogen peroxide (DakoCytomatation) before incubation with the primary antibody for 12 hours at 4° C. Then, the sections were washed with PBS and incubated with an anti-mouse IgG antibody conjugated with peroxidase (DakoCytomatation) for 30 minutes at room temperature and the signal was detected using 3,3-diaminobenzidine (DakoCytomatation). After washing the sections in distilled water, they were counterstained with hematoxylin (Roqué et al., *Arterioscler Thromb Vasc Biol* 20, 335-342, 2000) and observed under a microscope.

Finally, both in the VSMCs in contractile phenotype and in the VSMCs in culture the functional contribution of the Kv1.3 channels to the membrane currents was studied by means of the patch-clamp technique in the whole-cell configuration with the previously described protocols (see Example 1 and also Miguel-Velado et al., Circ Res 97, 1280-1287, 2005). The blockers used were correolide at a concentration of 10 μM (kindly supplied by Merck laboratories), 10 nM Margatoxin (obtained from Alomone labs) (FIG. 6) and PAP-1 10 nM (obtained from Sigma). The drugs were prepared at the final concentrations indicated in the saline solution of the bath following the supplier's instructions and were applied to the cells for a period of 1-2 minutes. The currents were recorded before applying the drug (control) and in the presence of the drug, and the percentage of reduction in the amplitude of the currents induced by different blockers was calculated.

Results:

The analysis of the expression of the mRNA of the Kv1.3 channel shows a very significant increase of the expression levels in the two proliferation conditions (culture and endoluminal lesion) with respect to the contractile cells as illustrated in FIG. 4.

The study of the expression of the Kv1.3 protein showed that whereas only a small fraction of the VSMCs in contractile phenotype were labeled with the antibody against Kv1.3, almost all the VSMCs in culture showed intense labeling (FIG. 5, panel A). Similar results were obtained with the immunohistochemistry with the anti-Kv1.3 antibody in femoral artery sections (FIG. 5, panel B). The labeling in the control arteries, without lesion and therefore with VSMCs in contractile phenotype was scarce and limited to the medial layer, whereas an increase of proliferation (intimal hyperplasia) and an increase of the number of immunopositive cells both in the neointima and in the muscle layer are observed after the endoluminal lesion. The quantification of several experiments performed in different animals confirmed a significant increase of the labeled area in the damaged arteries (FIG. 5, panel B).

Finally, the study of the functional expression of the Kv1.3 channels recorded with electrophysiological techniques allowed confirming that this increase of the expression of the mRNA and the protein of Kv1.3 in VSMCs in proliferative phenotype reflects an increase of the functional expression of the channels, since the currents mediated by Kv1.3 were significantly greater in VSMCs in culture than in freshly dissociated, contractile VSMCs (FIG. 6).

As can be seen in panel B of FIG. 6, the effect of these blockers (and therefore the fraction of the current which represent the Kv1.3 channels) was significantly greater in the VSMCs in culture in all the cases. For example, in the case of Margatoxin, the current blocked by this drug was 10.6±2.03 of the Kv current in the contractile VSMCs and 58.15±4.54 of the Kv current in the VSMCs in culture, and in the case of PAP-1 (i.e., the Kv1.3 channels contribute with 10% of the total current in the differentiated cells and almost 60% of the total current in the cells in culture.

All these data as a whole point to an increase of the contribution of these channels to the currents of proliferating VSMCs, and clearly show that these channels could represent valuable therapeutic tools for blocking proliferation since the increase in their expression participates in the changes leading the VSMCs to proliferate.

Example 4

Effect of the Specific Blocking of Kv1.3 Channel with Margatoxin and with PAP-1 on the Rate of Migration and Proliferation of the VSMCs in Culture Methods:

The migration studies have been performed in cultures of smooth muscle cells obtained from explants of confluent human uterine arteries, maintained in DMEM culture medium supplemented with 20% fetal bovine serum, 100 U/ml of penicillin and streptomycin and 2 mM of L-glutamine at 37° C. in a humidified incubator with a 5% $CO_2$ atmosphere. In these cultures, a small surface of the single layer is scraped by means of the tip of a sterile P10 pipette creating a space without cells and they are left for 24-48 hours in the same culture medium but without supplementing with fetal bovine serum to block proliferation. The area of the surface without cells created by the tip of the pipette was quantified by means of the image analysis software of the Image J program, measuring it at 0, 24 and 48 hours. The cell-free area at 0 hours was taken as control and the area at 24 or 48 hours is expressed as a fraction of the control area, which allows determining the degree of migration as the percentage of cell-free area at 24 or 48 hours with respect to the cell-free area at 0 hours (100%). The migration in these cultures in control situation and in the presence of margatoxin (10 nM) or PAP-1 (10 nM) was studied. The drugs are prepared in sterile saline solution at a concentration of 10 µM and added to the culture medium without serum (1 µl/ml to obtain the final concentration of 10 nM.

For the proliferation studies, the fraction of cells incorporating 5-bromo-2'-deoxyuridine (BrdU) was determined. BrdU is a thymidine analog which can be incorporated in its place for the synthesis phase of the cell cycle. The cells incorporating BrdU can be detected by means of observation under a fluorescence microscope upon using a monoclonal antibody against this molecule and a secondary antibody conjugated with a fluorochrome. The assay was performed with a commercial kit (5-Bromo-2'-deoxy-uridine labeling and Detection Kit I; Roche Applied Science, Germany). The human uterine artery smooth muscle cells were grown for 48 hours in glass coverslips 12 mm in diameter in DMEM medium supplemented with serum and antibiotics as has been previously described, until reaching a confluence close to 50%. At this time, the coverslips are maintained for 24 hours at 37° C. and in 5% $CO_2$ atmosphere in culture medium with 5% fetal bovine serum (control), medium with 5% serum and 10 nM of PAP-1 and medium with 5% serum and 10 nM of Margatoxin, after which the BrdU incorporation assay is performed following the instructions of the commercial company. To quantify the results, the number of cells positive for BrdU with respect to the total number of cells in the field (which is determined by labeling the nuclei with the DAPI fluorescent dye) is counted in 10-20 fields in each experiment.
Results:

The migration of the VSMCs of the uterine artery was reduced significantly in the presence of these Kv1.3 channel blockers. The left panels of FIG. 7 show the images taken in a representative culture in which the effect of these two drugs on the migration of the VSMCs at 24 hours was studied, as well as average results (right panel).

In relation to the proliferation experiments, a reduction in the fraction of cells labeled with BrdU in the groups treated with the Kv1.3 channel blockers is also observed, indicating that blocking the channel inhibits proliferation (see FIG. 8).

These results indicate again that the increase of the expression of Kv1.3 is associated with the proliferation and migration of the cells in this preparation, in which the previous results showed that, like in the VSMCs of the mouse femoral artery, the proliferation induces an increase in the expression of Kv1.3 both in terms of mRNA and protein (Miguel-Velado et al., Circ Res 97, 1280-1287, 2005).

Example 5

Prophetical

Swine Animal Model for the Treatment of Restenosis

Methods:
Expandable stainless steel stents (Cordis Co) 18 mm in length covered with a thin layer of a poly-n-butyl methacrylate and polyethylene-vinyl acetate copolymer containing 200 µg of PAP-1 or 200 µg of ShK-L5 are used. The total weight of the polymer with the drug is about 500 µg and the drug:polymer ratio is 30%. The stents are packed individually, coded with a bar code (to do a double blind experiment) and sterilized with ethylene oxide.

36 stents (12 with the polymer alone, 12 with PAP and 12 with ShK) are implanted in 12 young pigs (25-35 kg) in the anterior descending or circumflex branches of the left coronary artery or in the right coronary artery (at a proportion of 3 stents per animal). The animals recover from the operation and are sent back to the animal house where they receive a normal diet supplemented with aspirin (325 mg/d). Blood samples of the animals are obtained at 6, 12, 24, 48 and 96 hours to determine the plasma levels of PAP and ShK. At 7 (n=4) or 28 days (n=8) the animals are euthanized after performing a coronary arteriography for the quantitative analysis. In one animal of each group (7 and 28 days), after euthanasia the coronary arteries are dissected, the stent is removed and the samples are frozen in liquid nitrogen in order to determine different markers by means of Western blot of the tissues and to determine the levels of PAP and ShK in the arterial wall. In the rest of the animals, immediately after euthanasia the hearts are collected and the coronary arteries are fixed by perfusion of formalin at 10% for 30 minutes. Then the coronary vessels are dissected and processed for their immunohistological and morphometric analysis performing sections of the area where the stent and the superior and inferior margins are located.

Figure 9:
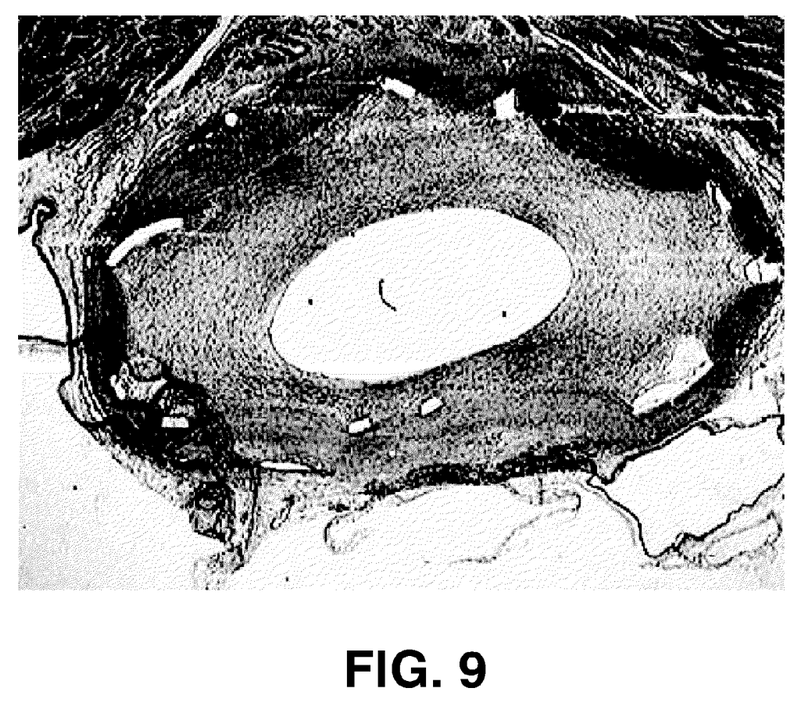
FIG. 9. Example of a micrograph of a section of a stained coronary vessel in which the different vascular layers can be distinguished to perform morphometric analyses, measuring the degree of endothelialization of the area of the stent, the VSMC content in the intima and its thickness in relation to the thickness of the vessel and the area of the lumen.

A morphometric analysis is performed measuring the degree of endothelialization of the stent area, the content of VSMCs in the intima and its thickness in relation to the thickness of the vessel and the lumen area (see FIG. 9).

The pharmacokinetics studies show that the blood levels of PAP-1 and ShK are maximal in the initial measure at 6 hours after implanting the stent (about 3 ng/ml) and decrease and are maintained below the limit of detection at 4 days (<0.2 ng/ml). The content of PAP and ShK in the arterial tissue is 97 and 83 ng/artery at 7 days and 30 and 25 ng/artery at 28 days.

The morphometric studies indicate that differences in the level of endothelialization between the control stents and the stents with the blockers are not observed. However, the number of VSMCs in the intima significantly decreased in the arteries with the stents treated with PAP and ShK, as did the degree of stenosis (45% in control against 27% in the presence of PAP-1 and 26.2% with ShK) and the intimal area (5.07 mm$^2$ in control against 2.23 mm$^2$ with PAP-1 and 2.06 mm$^2$ with ShK).

The determinations of the expression of marker proteins for the formation of the intima such as PCNa and pRb and for inflammation such as IL6 are quantified by means of Westernblot and quantified by densitometry. The results again show a significant reduction of the presence of all these markers in the arterial segments where the stents with the Kv1.3 blockers are placed, in which the levels of these proteins represent between 30 and 50% of the levels observed in the areas where the control stents are placed.

The results indicate that the method is efficient for reducing the proliferation of the intima and the inflammatory response without causing local immunological or allergic reactions. Similarly, the system for releasing the blockers has its effects locally but the circulating levels are undetectable, reducing the possibility of side effects. This type of approach could be considered for used in humans.

The invention claimed is:
1. A method for the treatment or inhibition of intimal hyperplasia in patients in need thereof comprising the administration of a Kv1.3 blocking substance, wherein the admin- istration of the Kv1.3 blocking substance results in the recovery or maintenance of the normal vascular structure.

2. The method of claim 1, wherein the blocking substance is a toxin selected from the group consisting of margatoxin, ShK toxin, psoralen, kaliotoxin, correolide, J123, derivatives thereof and combinations thereof.

3. The method of claim 1, wherein the blocking substance is selected from the group consisting of ShK-L5, PAP-1 or a combination thereof.

4. The method of claim 1 wherein said intimal hyperplasia is associated with restenosis, post-transplant chronic nephropathy, late by-pass occlusion, post-transplant coronary vasculopathy, equivalents thereof and combinations thereof.

5. A method of treatment of intimal hyperplasia comprising implanting a supplying device in an arterial vessel of an animal in need thereof, said supplying device comprising a Kv1.3 blocking substance, wherein the implantation of the supplying comprising the Kv1.3 blocking substance results in the recovery or maintenance of the normal vascular structure.

6. The method of claim 5, wherein said supplying device is a stent.

7. The method of claim 5, wherein said Kv1.3 channel blocker is selected from the group consisting of margatoxin, ShK toxin, psoralen, kaliotoxin, correolide, J123, derivatives thereof and combinations thereof.

8. The method of claim 7, wherein said blocking substance is selected from the group consisting of ShK-L5, PAP-1 or a combination thereof.

9. The method of claim 5, wherein said intimal hyperplasia is associated with restenosis, post-transplant chronic nephropathy, late by-pass occlusion, post-transplant coronary vasculopathy, equivalents thereof and combinations thereof.

\* \* \* \* \*